United States Patent
Fuller et al.

(10) Patent No.: US 10,766,883 B2
(45) Date of Patent: Sep. 8, 2020

(54) AMINOPYRAZOLES AS JANUS KINASE INHIBITORS

(71) Applicant: Merck Sharp & Dohme Corp., Rahway, NJ (US)

(72) Inventors: Peter Fuller, Boston, MA (US); Jason Brubaker, Cambridge, MA (US); Hongbo Zeng, Westford, MA (US); Joshua Close, Franklin, MA (US); Jonathan Young, Poway, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/468,465

(22) PCT Filed: Dec. 7, 2017

(86) PCT No.: PCT/US2017/064986
§ 371 (c)(1),
(2) Date: Jun. 11, 2019

(87) PCT Pub. No.: WO2018/111663
PCT Pub. Date: Jun. 21, 2018

(65) Prior Publication Data
US 2019/0330195 A1    Oct. 31, 2019

Related U.S. Application Data

(60) Provisional application No. 62/434,142, filed on Dec. 14, 2016.

(51) Int. Cl.
*C07D 405/04* (2006.01)
*C07D 405/14* (2006.01)

(52) U.S. Cl.
CPC ......... *C07D 405/04* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,922,741 A | 7/1999 | Davis et al. | |
| 9,394,282 B2 * | 7/2016 | Brubaker | C07D 413/12 |
| 2010/0048567 A1 | 2/2010 | Jia et al. | |
| 2014/0228348 A1 | 8/2014 | Brubaker et al. | |
| 2014/0235641 A1 | 8/2014 | Brubaker et al. | |

FOREIGN PATENT DOCUMENTS

| | | |
|---|---|---|
| WO | 2013041042 A1 | 3/2013 |
| WO | 2014146492 A1 | 9/2014 |

OTHER PUBLICATIONS

International Search Report and Written Opinion for PCT/US2017/64986, dated Feb. 23, 2018, 8 pages.
European Search Report, Application No. 17879816.1 dated May 27, 2020, 8 pages.

* cited by examiner

*Primary Examiner* — Kamal A Saeed
(74) *Attorney, Agent, or Firm* — Patricia A. Shatynski; John C. Todaro

(57) ABSTRACT

The instant invention provides compounds which are JAK inhibitors, and as such are useful for the treatment of JAK-mediated diseases such as rheumatoid arthritis, asthma, COPD and cancer.

20 Claims, No Drawings

AMINOPYRAZOLES AS JANUS KINASE INHIBITORS

CROSS REFERENCE TO RELATED APPLICATIONS

This application is a U.S. National Phase application under 35 U.S.C. § 371 of PCT Application No. PCT/US2017/064986, filed Dec. 7, 2017 which claims priority under 35 U.S.C. § 119(e) from U.S. Provisional Application Serial No. 62/434,142, filed on Dec. 14, 2016.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

A considerable body of literature has accumulated that link the JAK/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

Results from clinical trials with multi JAK inhibitors tofacitinib citrate (Xeljanz®, Pfizer) a JAK1/JAK2/JAK3 inhibitor and baricitinib (Lilly) a selective JAK1 and JAK2 inhibitor support the hypothesis that high levels of efficacy can be achieved through targeting JAK inhibition. (For tofacitinib studies see: Kremer et al., Arthritis Rheum. (2012) 64(5): 1487, "The safety and efficacy of a JAK inhibitor in patients with active rheumatoid arthritis"; Fleishmann R. et al., Int J. Rheum Dis. 2016 Jul. 24, "Tofacitinib in patients with active rheumatoid arthritis"; Fleischmann R. et al. NEJM (2012) 367:495-507, "Placebo controlled trial of tofacitinib monotherapy in rheumatoid arthritis"; and for baricitinib see, Greenwald, M. W. et al.; Arthritis & Rheum., Vol. 62, November 2010 Abst. Suppl. "A randomized dose-ranging, PBO-controlled study of TNCB028050, a selective JAK1 and JAK2 inhibitor, in subjects with active rheumatoid arthritis", respectively). However, dose limiting adverse events (AEs) have limited the efficacy and use of these agents. Significant hematopoietic AEs, specifically anemia, were observed in patients taking both tofacitinib and baricitinib, with a greater incidence and severity at higher doses. (See Yamaoka, K., Current Opinion Chem. Bio. (2016) 32:29-33; and Greenwald, M. W. et al.; Arthritis & Rheum., Vol. 62, November 2010 Abst. Suppl.).

The occurrence of anemia is believed to be due to inhibition of erythropoietin (EPO) signaling. EPO is a growth factor critical for red blood cell development that signals via JAK2. Inhibition of EPO also leads to an inability to recover from anemia of chronic disease. Approximately 40% of rheumatoid arthritis (RA) patients suffer from anemia of chronic disease (See, Masson, C. et al., Joint Bone Spine 78(2011):131-137, "Rheumatopid Anemia"; and Han et al., J. Rheumatol. (2007)34 (11):2177-2182), "Association of anemia and physical disability among patients with rheumatoid arthritis". The current treatment paradigm is to treat the inflammation that causes this anemia; however treatment with multi-JAK inhibitors that also inhibit EPO signaling cancels out the benefits on hemoglobin levels from treating the inflammation. Specific JAK1 inhibitors would not impact EPO signaling, would not be limited by anemia AEs, and would allow hemoglobin levels to rebound after inflammation was reversed.

Additional clinical evidence supporting the JAK1 hypothesis comes from tocilizumab (Actemra®, Hoffmann-La Roche), a humanized monoclonal antibody against the interleukin-6 (IL-6) receptor. IL-6 signals through JAK1 and JAK2 pathway. High levels of efficacy are achieved with this biologic agent without inducing anemia, and anemia of inflammation is successfully reversed (See Emery, P., et al., Ann. Rheum. Dis. (2008) 67:1516-1523, "IL-6 receptor inhibition with tocilizumab improves treatment outcomes in patients with RA refractory to anti-TNF biologicals: results of a 24-week multicenter randomized placebo-controlled trial"; and Hashizume, M. et al., Rheumatol. Int. (2010) 30(7):917-23), "Tocilizumab, a humanized anti-IL-6 receptor antibody, improved anemia in monkey arthritis by suppressing IL-6 induced hepcidin production".

There is a need to identify JAK1 specific inhibitors that do not impact EPO signaling in order to mitigate the occurrence of anemia adverse events.

WO 2013/041042 discloses pyrazole carboxamdines as Janus Kinase Inhibitors that are useful for the treatment of rheumatoid arthritis, asthma, COPD and cancer. WO 2013/041042 discloses compounds of the following formula:

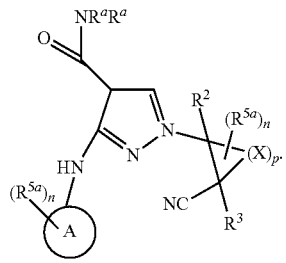

SUMMARY OF THE INVENTION

The present invention provides compounds which inhibit JAK1 while at the same time minimize EPO signaling inhibition. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds selected from:
3-((4-Chloro-3-methoxyphenyl)amino)-1-(4-cyanotetrahydro-2H-pyran-3-yl)-1H-pyrazole-4-carboxamide;
3-((4-chloro-3-(methylthio)phenyl)amino)-1-(4-cyanotetrahydro-2H-pyran-3-yl)-1H-pyrazole-4-carboxamide;
3-((4-cyano-3-methoxyphenyl)amino)-1-(4-cyanotetrahydro-2H-pyran-3-yl)-1H-pyrazole-4-carboxamide;
3-((4-cyano-3-(2-fluoropropan-2-yl)phenyl)amino)-1-(4-cyanotetrahydro-2H-pyran-3-yl)-1H-pyrazole-4-carboxamide; and
1-(4-cyanotetrahydro-2H-pyran-3-yl)-3-((3-methylbenzo[d]isoxazol-5-yl)amino)-1H-pyrazole-4-carboxamide;
or a pharmaceutically acceptable salt thereof.

Another embodiment of the invention provides compounds selected from
3-((4-Chloro-3-methoxyphenyl)amino)-1-((3R,4S)-4-cyanotetrahydro-2H-pyran-3-yl)-1H-pyrazole-4-carboxamide;
3-((4-chloro-3-(methylthio)phenyl)amino)-1-((3R,4S)-4-cyanotetrahydro-2H-pyran-3-yl)-1H-pyrazole-4-carboxamide;
3-((4-cyano-3-methoxyphenyl)amino)-1-((3R,4S)-4-cyanotetrahydro-2H-pyran-3-yl)-1H-pyrazole-4-carboxamide;
3-((4-cyano-3-(2-fluoropropan-2-yl)phenyl)amino)-1-((3R,4S)-4-cyanotetrahydro-2H-pyran-3-yl)-1H-pyrazole-4-carboxamide; and
1-((3R,4S)-4-cyanotetrahydro-2H-pyran-3-yl)-3-((3-methylbenzo[d]isoxazol-5-yl)amino)-1H-pyrazole-4-carboxamide;
or a pharmaceutically acceptable salt thereof.

The invention also encompasses pharmaceutical compositions containing one or more compounds of the present invention and methods for treatment or prevention of JAK mediated diseases using the compounds.

The invention is described using the following definitions unless otherwise indicated.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

"Celite®" (Fluka) diatomite is diatomaceous earth, and can be referred to as "celite".

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. Structural representations of compounds having substituents terminating with a methyl group may display the terminal methyl group either using the characters "CH₃", e.g. "—CH₃" or using a straight line representing the presence of the methyl group, e.g., "———", i.e., "⁂———CH₃" and "⁂———" and have equivalent meanings.

One embodiment of the invention is a compound selected from:
3-((4-Chloro-3-methoxyphenyl)amino)-1-(4-cyanotetrahydro-2H-pyran-3-yl)-1H-pyrazole-4-carboxamide;
3-((4-chloro-3-(methylthio)phenyl)amino)-1-(4-cyanotetrahydro-2H-pyran-3-yl)-1H-pyrazole-4-carboxamide; and
3-((4-cyano-3-methoxyphenyl)amino)-1-(4-cyanotetrahydro-2H-pyran-3-yl)-1H-pyrazole-4-carboxamide;
or a pharmaceutically acceptable salt thereof.

Another embodiment of the invention is a compound selected from:
3-((4-cyano-3-(2-fluoropropan-2-yl)phenyl)amino)-1-(4-cyanotetrahydro-2H-pyran-3-yl)-1H-pyrazole-4-carboxamide; and
1-(4-cyanotetrahydro-2H-pyran-3-yl)-3-((3-methylbenzo[d]isoxazol-5-yl)amino)-1H-pyrazole-4-carboxamide;
or a pharmaceutically acceptable salt thereof.

In a variant of this embodiment, the compound is 3-((4-Chloro-3-methoxyphenyl)amino)-1-(4-cyanotetrahydro-2H-pyran-3-yl)-1H-pyrazole-4-carboxamide, or a pharmaceutically acceptable salt thereof.

In another embodiment, the compound is 3-((4-chloro-3-(methylthio)phenyl)amino)-1-(4-cyanotetrahydro-2H-pyran-3-yl)-1H-pyrazole-4-carboxamide, or a pharmaceutically acceptable salt thereof.

In yet another embodiment, the compound is 3-((4-cyano-3-methoxyphenyl)amino)-1-(4-cyanotetrahydro-2H-pyran-3-yl)-1H-pyrazole-4-carboxamide, or a pharmaceutically acceptable salt thereof.

In another embodiment of the invention, the compound is 3-((4-cyano-3-(2-fluoropropan-2-yl)phenyl)amino)-1-(4-cyanotetrahydro-2H-pyran-3-yl)-1H-pyrazole-4-carboxamide, or a pharmaceutically acceptable salt thereof.

In another embodiment of the invention, the compound is 1-(4-cyanotetrahydro-2H-pyran-3-yl)-3-((3-methylbenzo[d]isoxazol-5-yl)amino)-1H-pyrazole-4-carboxamide, or a pharmaceutically acceptable salt thereof.

Another embodiment of the invention provides compounds selected from:
3-((4-Chloro-3-methoxyphenyl)amino)-1-((3R,4S)-4-cyanotetrahydro-2H-pyran-3-yl)-1H-pyrazole-4-carboxamide;
3-((4-chloro-3-(methylthio)phenyl)amino)-1-((3R,4S)-4-cyanotetrahydro-2H-pyran-3-yl)-1H-pyrazole-4-carboxamide; and
3-((4-cyano-3-methoxyphenyl)amino)-1-((3R,4S)-4-cyanotetrahydro-2H-pyran-3-yl)-1H-pyrazole-4-carboxamide;
or a pharmaceutically acceptable salt thereof.

One embodiment of the invention is a compound selected from:
3-((4-cyano-3-(2-fluoropropan-2-yl)phenyl)amino)-1-((3R,4S)-4-cyanotetrahydro-2H-pyran-3-yl)-1H-pyrazole-4-carboxamide; and
1-((3R,4S)-4-cyanotetrahydro-2H-pyran-3-yl)-3-((3-methylbenzo[d]isoxazol-5-yl)amino)-1H-pyrazole-4-carboxamide; or a pharmaceutically acceptable salt thereof.

Another embodiment of the invention is compound 3-((4-Chloro-3-methoxyphenyl)amino)-1-((3R,4S)-4-cyanotetrahydro-2H-pyran-3-yl)-1H-pyrazole-4-carboxamide; or a pharmaceutically acceptable salt thereof.

One embodiment of the invention is compound 3-((4-chloro-3-(methylthio)phenyl)amino)-1-((3R,4S)-4-cyanotetrahydro-2H-pyran-3-yl)-1H-pyrazole-4-carboxamide; or pharmaceutically acceptable salt thereof.

Another version of the invention is a compound 3-((4-cyano-3-methoxyphenyl)amino)-1-((3R,4S)-4-cyanotetrahydro-2H-pyran-3-yl)-1H-pyrazole-4-carboxamide; or a pharmaceutically acceptable salt thereof.

One embodiment of the invention is a compound 3-((4-cyano-3-(2-fluoropropan-2-yl)phenyl)amino)-1-((3R,4S)-4- cyanotetrahydro-2H-pyran-3-yl)-1H-pyrazole-4-carboxamide; or a pharmaceutically acceptable salt thereof.

Another embodiment is a compound 1-((3R,4S)-4-cyano-tetrahydro-2H-pyran-3-yl)-3-((3-methylbenzo[d]isoxazol-5-yl)amino)-1H-pyrazole-4-carboxamide; or a pharmaceutically acceptable salt thereof.

In one embodiment, the compounds of the instant invention are selective JAK1 inhibitors relative to JAK2 and JAK3. The determination of relative selectivity for a given compound of JAK1 inhibition is defined as the relative ratio of the (JAK2 $IC_{50}$ value/JAK1 $IC_{50}$ value) is at least about 9.

In one embodiment, the compounds of the instant invention are selective JAK1 inhibitors relative to JAK2 and JAK3 and the compounds of the instant invention minimize the inhibition of the EPO/JAK2/STAT5 pathway with human EPO. The determination of relative selectivity for a given compound of JAK1 inhibition that would not impact EPO signaling may be defined as the relative ratio of the (IL-6 IP value/EPO IP value) is at least about 10.

In yet another embodiment, for a given compound, the relative ratios of the (IL-6 IP value/EPO IP value) is at least about 15.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^3R^3)_2$—, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the present invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Diastereomeric mixtures can be separated into their individual diastereomers on the basis of their physical chemical differences by methods well known to those skilled in the art, such as, for example, by chromatography (e.g. chiral HPLC column) and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of the present invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the present invention can be prepared without undue experimentation by conventional techniques well known to those skilled in the art or by processes analogous to those described in the Schemes and Examples herein using appropriate isotopically-enriched reagents and/or intermediates.

Utilities

A compound of the present invention or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis *nodosa*, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of the present invention. In one embodiment such diseases include asthma and rheumatoid arthritis.

Another aspect of the present invention provides for the use of a compound of the present invention in the manufacture of a medicament for the treatment or prevention of a JAK-mediated diseases or disorder.

Dose Ranges

The magnitude of prophylactic or therapeutic dose of a compound of the present invention will, of course, vary with the nature and the severity of the condition to be treated and with the particular compound of the present invention and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration to humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of the present invention with a pharmaceutically acceptable carrier. For the treatment of any of the prostanoid mediated diseases compounds of the present invention may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized Metered Dose Inhaler (pMDI) which releases a metered dose of medicine upon each actuation. The formulation for pMDIs can be in the form of solutions or suspensions in halogenated hydrocarbon propellants. The type of propellant being used in pMDIs has shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry Powder Inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-200% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of the present invention may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of of the present invention are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compounds of the present invention may be co-administered with other therapeutic agents. Thus in another aspect the present invention provides pharmaceutical compositions for treating JAK mediated diseases comprising a therapeutically effective amount of a compound of the present invention and one or more other therapeutic agents. In particular, for the treatment of the inflammatory diseases rheumatoid arthritis, psoriasis, inflammatory bowel disease, COPD, asthma and allergic rhinitis a compound of the present invention may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Schemes and Examples

The abbreviations used herein have the following tabulated meanings. Abbreviations not tabulated below have their meanings as commonly used unless specifically stated otherwise.

| | |
|---|---|
| ACN | acetonitrile |
| ATP | adenosine triphosphate |
| MeCN | acetonitrile |
| BSA | Bovine serum albumin |
| BAST | bis(2-methoxyethyl)aminosulfur trifluoride |
| Chiral SFC | chiral super critical fluid chromatography |
| $CO_2$ | carbon dioxide |

-continued

| | |
|---|---|
| DBU | 1,8-diazabicyclo[5.4.0]undec-7-ene |
| DCM | dichloromethane |
| dinitrogen | $N_2$ |
| DMF | N,N-dimethylformamide |
| DMSO | dimethyl sulfoxide |
| DTT | Threo-1,4-dimercapto-2,3-butanediol (Cleland's reagent) |
| GST | Glutathione S-transferase |
| HCl | hydrogen chloride |
| HEPES | 4-(2-Hydroxyethyl)piperazine-1-ethane sulfonic acid, N-(2-Hydroxyethyl) piperazine-N'-(2-ethanesulfonic acid) |
| HPLC | high pressure liquid chromatography |
| HTRF | Homogeneous Time Resolved Fluorescence |
| IPA | 2-propanol |
| LRMS | low resolution mass spectrometry |
| MPLC | Medium pressure liquid chromatography |
| MeOH | methanol |
| $Pd_2(dba)_3$ | tris(dibenzylideneacetone)dipalladium(0) |
| $POCl_3$ | Phosphoryl chloride |
| SFC | Supercritical fluid chromatography |
| THF | tetrahydrofuran |
| Triton ™ X-100 | t-Octylphenoxypolyethoxyethanol, Polyethylene glycol tert-octylphenyl ether, Polyoxyethylene (10) isooctylphenyl ether |
| TMSCN | Trimethylsilyl cyanide |
| TMSOTf | Trimethylsilyl triflate |
| NMR | nuclear magnetic resonance |
| TLC | thin layer chromatography |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted.

Ambient temperature is 15-25° C.

Most compounds were purified by reverse-phase preparative HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

General procedures to prepare intermediates of the instant invention are described in Scheme 1. Where $R_1$ is methoxy, chloro or cyano; and $R_2$ is chloro, methylthio, methoxy or isopropyl.

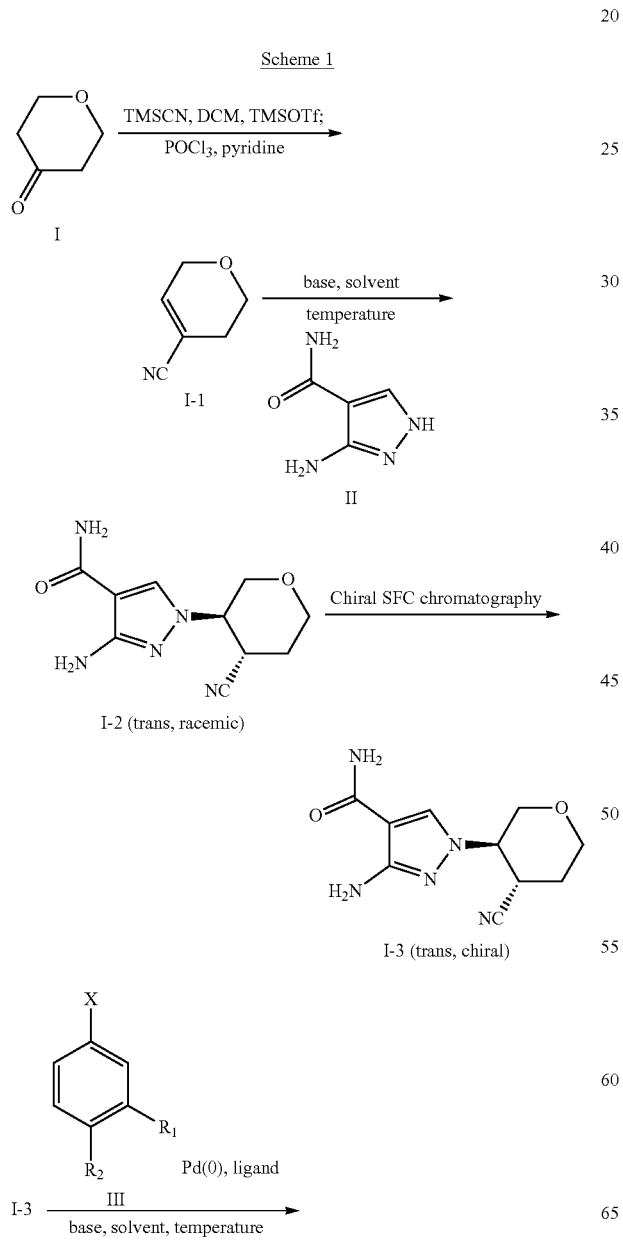

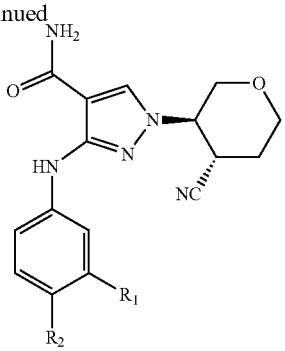

Intermediate 1

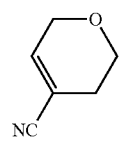

3,6-Dihydro-2H-pyran-4-carbonitrile (I-1)

To a solution of trimethylsilyl cyanide (Sigma-Aldrich, St. Louis, Mo., USA) (28.0 g, 288 mmol) in dichloromethane (100 mL) were sequentially added tetrahydro-4H-pyran-4-one (I) (Sigma-Aldrich, St. Louis, Mo., USA) (24 g, 243 mmol) and trimethylsilyl triflate (1.6 g, 7.2 mmol) at 0° C. The resulting solution was stirred at 0° C. for 1 hour before the addition of pyridine (300 mL) and phosphoryl chloride (110 g, 719 mmol). The mixture was refluxed for 12 hours, and then poured into a mixture of 2 N aqueous hydrochloric acid solution (600 mL), crushed ice (180 mL) and ether (600 mL) at 0° C. The mixture was vigorously stirred for 15 minutes, and then extracted with ether (3×1 L). All the organic solution was washed with brine (2×300 mL), dried over anhydrous sodium sulfate, filtered and concentrated in vacuo. The crude residue was purified by flash column chromatography with 1-2% ethyl acetate in hexane to afford the title compound, I-1, as an oil. $^1$H NMR (300 MHz, CDCl$_3$) δ 6.62-6.59 (m, 1H), 4.29-4.21 (m, 2H), 3.78 (t, J=5.4 Hz, 2H), 2.34-2.30 (m, 2H).

Intermediate I-3

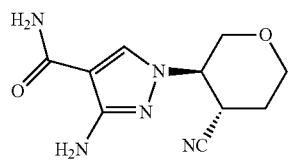

3-Amino-1-((3R,4S)-4-cyano-3-v)-1H-pyrazole-4-carboxamide (I-3)

A mixture of 3-amino-1H-pyrazole-4-carboxamide (II) (Enamine Ltd, Ukraine) (804 g, 4.59 mol), 3,6-dihydro-2H- pyran-4-carbonitrile (I-1, 1000 g, 9.17 mol) and DBU (2435 g, 16 mol) in ethanol (800 mL) was stirred at 70° C. overnight under nitrogen, and then concentrated in vacuo. The crude residue was purified by silica gel flash column chromatography with 2-5% methanol in dichloromethane to afford the a racemic trans, racemic intermediate, 1-2, as a solid. Chiral separation: 380 g of trans, racemic I-2 was dissolved in ACN/MeOH (1:1) to a concentration of 25 mg/mL. Injections of 16 mL were made on a Thar 350 preparative SFC (Thar Instruments, Inc., Pittsburgh, Pa., USA) (Column: ChiralPak® IC-10 μM, 300×50 mm (Daicel Corp., West Chester, Pa., USA); Mobile phase: 45% 2-propanol, 55% $CO_2$; Flow rate: 220 mL/min; Column temperature: 38° C.). After separation, the fractions were dried by rotary evaporation. The second (slower eluting) peak, intermediate, I-3, was used to prepare the following compounds.

$^1$H NMR (500 MHz, DMSO-$d_6$) δ 8.03 (s, 1H), 7.36 (brs, 1H), 6.80 (brs, 1H), 5.36 (s, 2H), 4.86-4.31 (td, J=10.5, 4.5 Hz, 1H), 3.91-3.88 (dd, J=11.5, 4.5 Hz 1H), 3.86-3.83 (m, 1H), 3.53-3.50 (m, 2H), 3.39-3.33 (td, J=11.5, 2 Hz, 1H), 2.10-2.07 (m, 1H), 1.95-1.87 (m, 1H). LRMS (ESI) calc'd for $C_{10}H_4N_5O_2$ [M+H]$^+$: 236, Found: 236.

Example 1

(Ex-1)

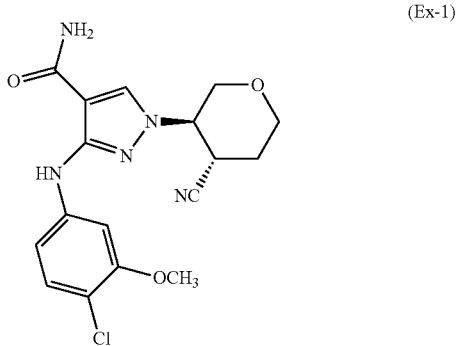 [SMILES: COc1cc(Nc2nn([C@H]3COCC[C@@H]3C#N)cc2C(N)=O)ccc1Cl]

3-((4-Chloro-3-methoxyphenyl)amino)-1-((3R,4S)-4-cyanotetrahydro-2H-pyran-3-yl)-1H-pyrazole-4-carboxamide (Ex-1)

A 500 mL 3-neck flask was fitted with a reflux condenser and J-KEM thermocouple (J-Kem®, Scientific, Inc.; St. Louis, Mo., USA), then charged with 3-amino-1-((3R,4S)-4-cyanotetrahydro-2H-pyran-3-yl)-1H-pyrazole-4-carboxamide (1-3) (10.0 g, 42.5 mmol), 5-bromo-2-chloroanisole (14.1 g, 63.7 mmol), potassium acetate (6.26 g, 63.8 mmol) and 2-propanol (150 ml). The reactions mixture was sparged with dinitrogen gas for 20 min, then Pd$_2$(dba)$_3$ (1.95 g, 2.13 mmol) and 2-di-tert-butylphosphino-2',4',6'-triisopropylbiphenyl (2.00 g, 4.71 mmol) were added. The reaction mixture was then heated to 80° C. for 16.5 h. After cooling to 23° C., acetone (150 mL) was added and the mixture was stirred for 10 min, then filtered through Celite® with acetone elution. The filtrate was concentrated onto silica gel in vacuo and purified via flash-column chromatography (ISCO® (Teledyne Isco, London, Nebraska, USA) 220 g cartridge, gradient elution with 3-6% methanol-dicholoromethane). The product-containing fractions were concentrated to afford 3-((4-chloro-3-methoxyphenyl)amino)-1-((3R,4S)-4-cyanotetrahydro-2H-pyran-3-yl)-1H-pyrazole-4-carboxamide, Ex-1, as a solid.

$^1$H NMR (600 MHz, DMSO-d6): δ 9.24 (s, 1H), 8.31 (s, 1H), 7.75 (s, 1H), 7.48 (d, J=2.3 Hz, 1H), 7.23-7.22 (m, 2H); 7.08 (dd, J=8.6, 2.3 Hz, 1H), 4.59 (td, J=10.2, 4.4 Hz, 1H), 4.05 (dd, J=11.3, 4.4 Hz, 1H), 3.94-3.87 (m, 4H), 3.68-3.64 (m, 2H), 3.44 (t, J=11.7 Hz, 1H), 2.16 (d, J=13.3 Hz, 1H), 1.98 (qd, J=12.3, 4.3 Hz, 1H). LRMS (ESI) calc'd for $C_{17}H_{19}ClN_5O_3$[M+H]$^+$: 376, Found: 376.

The following Examples shown in Table 1 were prepared according to the Generic Scheme following similar procedures described above for Example 1, which can be achieved by those of ordinary skill in the art of organic synthesis.

TABLE 1

| Example | Structure | IUPAC Name | Exact Mass [M + H]$^+$ |
|---|---|---|---|
| Ex-1 | 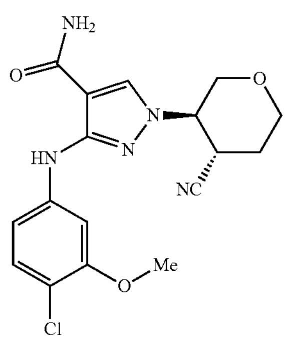 [SMILES: COc1cc(Nc2nn([C@H]3COCC[C@@H]3C#N)cc2C(N)=O)ccc1Cl] | 3-((4-Chloro-3-methoxyphenyl)amino)-1-((3R,4S)-4-cyanotetrahydro-2H-pyran-3-yl)-1H-pyrazole-4-carboxamide | Cal'd 376; Found 376 |

TABLE 1-continued

| Example | IUPAC Name | Exact Mass [M + H]+ |
|---|---|---|
| Ex-2 | 3-((4-chloro-3-(methylthio)phenyl)amino)-1-((3R,4S)-4-cyanotetrahydro-2H-pyran-3-yl)-1H-pyrazole-4-carboxamide | Cal'd 392; Found 392 |
| Ex-3 | 3-((4-cyano-3-methoxyphenyl)amino)-1-((3R,4S)-4-cyanotetrahydro-2H-pyran-3-yl)-1H-pyrazole-4-carboxamide | Cal'd 367; Found 367 |
| Ex-4 | 3-((4-cyano-3-isopropylphenyl)amino)-1-((3R,4S)-4-cyanotetrahydro-2H-pyran-3-yl)-1H-pyrazole-4-carboxamide | Cal'd 379; Found 379 |
| Ex-5 | 1-((3R,4S)-4-cyanotetrahydro-2H-pyran-3-yl)-3-((3-methylbenzo[d]isoxazol-5-yl)amino)-1H-pyrazole-4-carboxamide | Cal'd 367; Found 367 |

Biological Assays

JAK Biochemical HTRF Enzyme Assay Protocol

The ability of compounds to inhibit the activity of JAK1, JAK2, JAK3, and Tyk2 was measured using a recombinant purified GST-tagged catalytic domain for each enzyme (In-Vitrogen/Life Technologies/ThermoFisher Scientific Inc., Waltham, Mass., USA; catalogue numbers: M4290(JAK1), M4290(JAK2), M4290(JAK3), M4290(Tyk2)) in an HTRF format biochemical assay. The reactions employed a common peptide substrate, LCB-EQEDEPEGDYFEWLW-NH2 (Merck Sharp & Dohme, Kenilworth, N.J., USA).

The basic assay protocol is as follows: First, 250 nL of diluted compounds in DMSO were dispensed into the wells of a dry 384-well Black plate (GreinerFluotrac™ catalog number: 781076; Greiner Bio-One GmbH, Frickenhausen, Germany) using a Labcyte Echo® 555 acoustic dispenser (Clarcyte, Inc, Sunnyvale, Calif., USA). Subsequent reagent additions employed an Agilent™ Bravo™ liquid handling system (Aligent Technologies, Santa Clara, Calif., USA). Next, 18 µL of 1.11× enzyme and 1.11× substrate in 1× assay buffer (Invitrogen kinase buffer catalogue number PV3189 (Invitrogen™/Life Technologies/ThermoFisher Scientific Inc., Waltham, Mass., USA), 2 mM DTT, 0.05% BSA) were added to the wells and shaken and then preincubated for 30 minutes at ambient temperature to allow compound binding to equilibrate. After equilibration, 2 µL of 10×ATP in 1× assay buffer was added to initiate the kinase reaction and the plates were shaken and then incubated at ambient temperature for 120 minutes. At the end of the incubation, 20 µL of 2× stop buffer (Streptavidin-Dylight 650/100 mL catalogue number: 8454B (Invitrogen™/Life Technologies/ThermoFisher Scientific Inc., Waltham, Mass., USA); Europium-tagged pY20 antibody (PerkinElmer™ catalogue number: AD0067 (PerkinElmer™, Waltham, Mass., USA)); EDTA; HEPES; and Triton™ X-100 (Sigma-Aldrich, St. Louis, Mo., USA) was added to quench the reaction. Plates were shaken and centrifuged and then incubated 60 minutes at ambient temperature and then read on a EnVision™ multi-label plate reader (PerkinElmer™, Waltham, Mass., USA) ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final Reaction Conditions were:

| Enzyme | Enzyme Conc. (nM) | Substrate Conc. (µM) | ATP Conc. (µM) | Eu-pY20 Conc. (nM) | SA-Dylight Conc. (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM. The final DMSO concentration was adjusted to 0.25%.

Assay Performance and Data Quality Control

Performance of enzyme assays was tracked by calculating minium significant ratio (MSR) values acoss assay runs for man- and selective-JAK reference molecules:

| Reference Compound | Structure | Name | Source |
|---|---|---|---|
| 1 | 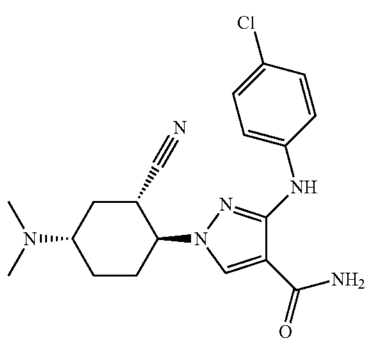 [SMILES: CN(C)[C@H]1CC[C@H](n2cc(C(N)=O)c(Nc3ccc(Cl)cc3)n2)[C@@H](C#N)C1] | 3-[(4-chlorophenyl)amino]-1-[(1S,2S,4S or 1R,2R,4R)-2-cyano-4-(dimethylamino)cyclohexyl]-1H-pyrazole-4-carboxamide | WO2013/040863, page 225, compound 28-117 |
| 2 | 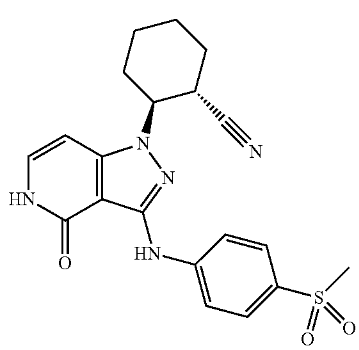 [SMILES: CS(=O)(=O)c1ccc(Nc2nn([C@H]3CCCC[C@@H]3C#N)c3cc[nH]c(=O)c23)cc1] | (1S,2S)-2-(3-{[4-(methylsulfonyl)phenyl]amino}-4-oxo-4,5-dihydro-1H-pyrazolo[4,3-c]pyridin-1-yl)cyclohexanecarbonitrile | WO2014/146490, page 163, compound 3-5 |

Potencies for Reference Compound No. 1, a JAK1 selective, were: JAK1 IC50=1.47 nM+/−0.40, N=392; JAK2 IC50=19.04+/−4.15 nM, N=393; JAK3 IC50=1351.45 nM+/−129.93, N=398 and TYK2 IC50=13.96 nM+/−3.17, N=394.

Potencies for Reference Compound No. 2, a JAK1 pan-inhibitor, were: JAK1 IC50=0.17 nM+/−0.06, N=399; JAK2 IC50=1.00+/−0.29 nM, N=400; JAK3 IC50=21.95 nM+/−6.08, N=404 and TYK2 IC50=0.28 nM+/−0.09, N=401.

Cell Pathway Engagement JAK Assays

Inhibition of the activity of JAK kinases (JAK1, JAK2, JAK3 and TYK2) in intact cells was quantified in antagonist mode using CellSensor® transcriptional reporter technology (Life Technologies/ThermoFisher Scientific Inc., Waltham, Mass., USA; https://www.thermofisher.com/us/en/home/industrial/pharma-biopharma drug-discovery-development/target-and-lead-identification-and-validation/pathway-biology/cellular-pathway-analysis/cellsensor-cell-lines.html), in three independent cell lines engineered to detect IL4, IL6 and EPO signaling. In brief, CellSensor® cell lines (see details below for each assay) carrying a stably integrated β-Lactamase reporter gene under control of specific cis-regulatory STAT elements responsive to the pathway being monitored were pre-treated with test compounds serially diluted in DMSO (see preparation and dosing of compounds and agonist cytokines section). Following incubation with compounds, IL4, IL6, or EPO were added to each cognate cell line at a concentration equal to a dose necessary to achieve 80% of the maximal response (EC80).

After cytokine stimulation, cellular levels of β-Lactamase activity were detected in situ using LiveBLAzer™ Loading Kit (LiveBLAzer™-FRET B/G substrate, CCF4-AM from Life Technologies/ThermoFisher Scientific Inc., Waltham, Mass., USA), where fluorescence of the substrate (emitting fluorescence at 405 nm) and cleaved product (emitting fluorescence at 488 nm) were quantified in an Acumen Explorer ex3 reader (TTP Labtech, Cambridge Mass. USA). Normalized fluorescence values reporting percentage inhibition of test compounds treated wells were plotted against the Log value of the concentration of each of ten doses selected to build a dose response curve (DRC) using a 4-parameter fit dose response equation to calculate the concentration necessary to achieve 50% inhibition of the maximal activity (IC50, or potency value) using internally developed assay data analyzer software (Merck Frosst Canada & Co—2003, Kingston, Ontario, Canada) and/or commercially available data analyzer software, ActivityBase™, (https://www.idbs.com/en/platform-products/activitybase/activitybase-for-biology/; IDBS, Guildford, Surrey, UK)

Percentage inhibition was calculated as function of the levels of beta lactamase measured in DMSO control treated wells, 0% inhibition, vs. levels of β-Lactamase in wells treated with a dose of a pan-JAK inhibitor sufficient to achieve 100% blockade of β-Lactamase production. Incubation with compounds, cytokines and LiveBLAzer™ were carried out at 37° C. in a tissue culture incubator maintained at 90% humidity and 5% $CO_2$.

Agonist and cell line pairings used to quantify functional inhibition of JAK regulated pathways were as follows:

Interleukin 4 (IL4)—JAK1/JAK3—STAT6 Pathway

CellSensor® STAT6-bla Ramos-1 (RA-1) cells carrying a stably integrated β-Lactamase reporter gene under control of the STAT6 Response Element (STAT6).

Interleukin 6 (IL6)—JAK1/JAK2—STAT4 Pathway

CellSensor™ SIE-bla ME-180 cells carrying a stably integrated β-Lactamase reporter gene under control of the Sis-Inducible Element (SIE).

Erythropoietin (EPO)—JAK2—STAT5 Pathway

CellSensor irf1-bla TF-1 cells carry a stably integrated β-Lactamase reporter gene under control of the STAT5 Response Elements present in the Interferon Regulatory Factor I (IRF1) gene promoter.

Preparation and Dosing of Test Compounds and Cytokines 10 mM compound as stock solutions prepared in DMSO were serially diluted 1:3, ten times, in DMSO using a Tecan Freedom EVO® 2 200 automated liquid handler (Tecan Group, Ltd., Mannedorf, Switzerland) in Echo® Qualified 384-Well Polypropylene Microplate (384PP), flat bottom, clear (Labcyte, Cat# P-05525; Labcyte Inc., Sunnyvale, Calif., USA). Sixty nL of each dose of compound were dispensed using an Echo® Acoustic Dispenser 550 (Labcyte Inc.) in a dry Corning® 384 Well Flat Clear Bottom Black Polystyrene TC-Treated Microplates (Corning Cat#3712, Corning Incorporated, Corning, N.Y., USA). Each CellSensor® cell line was subsequently plated as per supplier's instructions (30,000 cells in 32 μL/well) and mixed with the compound. Following a 60 minute incubation, cells were subsequently stimulated by addition of 8 μL of cognate cytokine (EC80 dose of IL4, IL6 and EPO) and incubated for an additional 3 hours, before adding LiveBLAzer™-FRET B/G substrate. Final doses of compound tested were: 14977; 4992; 1664; 554; 184; 61.6; 20.5; 6.8; 2.3 and 0.76 nM. The final DMSO concentration was kept at 0.15%.

Assay Performance and Data Quality Control:

Three parameters were used to validate quality of each individual assay run and to ensure development of narrow structure activity relationship (SAR) which enabled discerning differences between compounds whose potency varied by as low 3-4 folds:

(A) To verify that stimulation with cytokine was within the acceptable +/−5% of the dose necessary to achieve 80% stimulation, EC80, a 16 points agonist dose response curve (DRC) was included in every plate and this DRC was used to back calculate the level of stimulation reached across the plate. Top doses of the DRCs were: 80 ng/mL for LA, 500 ng/mL for IL6 and 100 ng/mL for EPO.

(B) DRCs for two reference compounds were included in each assay plate containing a total of 32 compounds per plate:
Reference Compound No. 1, a JAK1 selective molecule, twelve fold more potent in the IL6 CellSensor assay: IC50=51.9+/−23.6 nM, N=627 over the EPO CellSensor assay: IC50=623.5+/−132.3 nM, N=617. Activity in the IL4 CellSensor assay was: IC50=25.7+/−8.4 nM, N=307

Reference Compound No. 2, a pan-JAK inhibitor, that exhibited potency within two to three fold across all three assays. IL6/JAK1-JAK2 assay: IC50=21+/−9.1 nM, N=652 over EPO/JAK2 assay: IC50=39.5+/−12.4 nM, N=626 and IL4 CellSensor assay: IC50=11.1+/−3.4 nM, N=308

(C) Assay reproducibility across replicate plates and independent runs was monitored by calculating minimal significant ratio (MSR, see Eastwood et al., "The Minimum Significant Ratio: A Statistical Parameter to Characterize the Reproducibility of Potency Estimates from Concentration-Response Assays and Estimation by Replicate-Experiment Studies", J Biomol Screen 2006, (11) April 253-261) tracking IC50 potency values for both reference compounds.

Biological Data

Examples of the instant invention were evaluated in JAK1 and JAK2 in vitro binding assays as described above. Additionally, the Examples of the instant invention were evaluated in IL-6/JAK1 pathway reporter and the EPO/JAK2 pathway reporter in vitro binding assays as described above.

The IL-6 assay identifies agents that inhibit the beta-lactamase reporter activity initiated through stimulation of the IL-6R/JAK1/2/Stat3 pathway with recombinant human IL-6. The EPO assay identifies agents that inhibit the beta-lactamase reporter activity initiated through stimulation of the EPO/Jak2/Stat5 pathway with human EPO. Inhibition of EPO signaling leads to an inability to recover from anemia of chronic disease. To avoid possible anemia adverse events, it would be beneficial to find an agent that maximizes the inhibition of the IL-6R/JAK1/2 Stat3 pathway but does not significantly inhibit EPO/JAK2/Stat5 pathway. That is, it is desirable for the EPO/IL-6 IC50 ratios to be a relatively large number.

Table 2 provides a summary of the JAK1, JAK2, IL-6 and EPO inhibitory activities of the compounds of the present invention and selected compounds from international patent application publication number WO2013/041042, entitled "Pyrazole Carboxamides as Janus Kinase Inhibitors" and filed on Sep. 21, 2012. Specifically in Table 2, Comparative Ex-1, Comparative Ex-2, Comparative Ex-3 and Comparative Ex-4 respectively correspond to exemplified compounds 9-4, 9-10, 9-3 and 9-35 disclosed in WO2013/041042.

The compounds of the present invention exhibit favorable physicochemical and pharmacodynamics properties. Of particular interest, Table 2 reveals that the JAK2/JAK1 ratios of the presently claimed compounds possess potent JAK1 IC50s as compared to JAK2 IC50s. While exhibiting excellent JAK1 selectivity, surprisingly, the compounds of the present invention also demonstrate favorable EPO/IL-6 ratios that are greater than or equal to 16. These ratios indicate that the compounds of the present invention surprisingly and unexpectedly exhibit a desirable sub-nanomolar JAK1 inhibitory profile while also mitigating the inhibition of the EPO/JAK2/Stat5 pathway. By contrast, the comparative compounds, do not demonstrate the combination of high JAK1 selectivity and favorable EPO/IL-6 ratio profiles.

TABLE 2

| Example Number | Compound | JAK1 IC50 (nM) | JAK2 IC50 (nM) | JAK2/1 | IL-6 IP (nM) | EPO IP (nM) | EPO/IL-6 |
|---|---|---|---|---|---|---|---|
| Comp. Ex-1 9-4 | 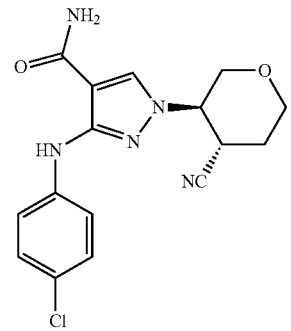 [SMILES: N#C[C@H]1CCOC[C@@H]1n1cc(C(N)=O)c(Nc2ccc(Cl)cc2)n1] | 0.17 | 1.92 | 11 | 14 | 132 | 9 |
| Comp. Ex-2 9-10 | 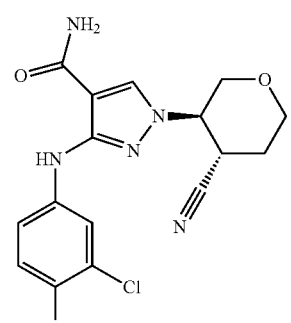 | 2.09 | 23.4 | 11 | 69 | 2166 | 31 |

TABLE 2-continued

| Example Number | Compound | JAK1 IC50 (nM) | JAK2 IC50 (nM) | JAK2/1 | IL-6 IP (nM) | EPO IP (nM) | EPO/IL-6 |
|---|---|---|---|---|---|---|---|
| Comp. Ex-3 9-3 | (structure) | 0.16 | 1.35 | 8 | 14 | 80 | 6 |
| Ex-1 | (structure) | 0.12 | 3.88 | 32 | 15 | 280 | 19 |
| Ex-2 | (structure) | 0.25 | 5.48 | 22 | 22 | 649 | 30 |
| Comp. Ex-4 9-35 | (structure) | 0.15 | 1.24 | 8 | 14 | 89 | 6 |

TABLE 2-continued

| Example Number | Compound | JAK1 IC50 (nM) | JAK2 IC50 (nM) | JAK2/1 | IL-6 IP (nM) | EPO IP (nM) | EPO/IL-6 |
|---|---|---|---|---|---|---|---|
| Ex-3 | (structure) | 0.07 | 3.28 | 49 | 19 | 431 | 23 |
| Ex-4 | (structure) | 0.49 | 9.7 | 20 | 47 | 744 | 16 |
| Ex-5 | (structure) | 0.16 | 3.04 | 19 | 17 | 309 | 18 |

What is claimed is:

1. A compound selected from:
3-((4-Chloro-3-methoxyphenyl)amino)-1-(4-cyanotetrahydro-2H-pyran-3-yl)-1H-pyrazole-4-carboxamide;
3-((4-chloro-3-(methylthio)phenyl)amino)-1-(4-cyanotetrahydro-2H-pyran-3-yl)-1H-pyrazole-4-carboxamide;
3-((4-cyano-3-methoxyphenyl)amino)-1-(4-cyanotetrahydro-2H-pyran-3-yl)-1H-pyrazole-4-carboxamide;
3-((4-cyano-3-(2-fluoropropan-2-yl)phenyl)amino)-1-(4-cyanotetrahydro-2H-pyran-3-yl)-1H-pyrazole-4-carboxamide; and
1-(4-cyanotetrahydro-2H-pyran-3-yl)-3-((3-methylbenzo[d]isoxazol-5-yl)amino)-1H-pyrazole-4-carboxamide;
or a pharmaceutically acceptable salt thereof.

2. A compound according to claim 1, selected from:
3-((4-Chloro-3-methoxyphenyl)amino)-1-((3R,4S)-4-cyanotetrahydro-2H-pyran-3-yl)-1H-pyrazole-4-carboxamide;
3-((4-chloro-3-(methylthio)phenyl)amino)-1-((3R,4S)-4-cyanotetrahydro-2H-pyran-3-yl)-1H-pyrazole-4-carboxamide;
3-((4-cyano-3-methoxyphenyl)amino)-1-((3R,4S)-4-cyanotetrahydro-2H-pyran-3-yl)-1H-pyrazole-4-carboxamide;
3-((4-cyano-3-(2-fluoropropan-2-yl)phenyl)amino)-1-((3R,4S)-4-cyanotetrahydro-2H-pyran-3-yl)-1H-pyrazole-4-carboxamide; and
1-((3R,4S)-4-cyanotetrahydro-2H-pyran-3-yl)-3-((3-methylbenzo[d]isoxazol-5-yl)amino)-1H-pyrazole-4-carboxamide;
or a pharmaceutically acceptable salt thereof.

3. A compound according to claim 1 which is 3-((4-Chloro-3-methoxyphenyl)amino)-1-(4-cyanotetrahydro-2H-pyran-3-yl)-1H-pyrazole-4-carboxamide, or a pharmaceutically acceptable salt thereof.

4. A compound according to claim 2, which is 3-((4-Chloro-3-methoxyphenyl)amino)-1-((3R,4S)-4-cyanotetrahydro-2H-pyran-3-yl)-1H-pyrazole-4-carboxamide, or a pharmaceutically acceptable salt thereof.

5. A compound according to claim 1, which is 3-((4-chloro-3-(methylthio)phenyl)amino)-1-(4-cyanotetrahydro-2H-pyran-3-yl)-1H-pyrazole-4-carboxamide, or a pharmaceutically acceptable salt thereof.

6. A compound according to claim 2, which is 3-((4-chloro-3-(methylthio)phenyl)amino)-1-((3R,4S)-4-cyano-tetrahydro-2H-pyran-3-yl)-1H-pyrazole-4-carboxamide, or a pharmaceutically acceptable salt thereof.

7. A compound according to claim 1, which is 3-((4-cyano-3-(2-fluoropropan-2-yl)phenyl)amino)-1-(4-cyano-tetrahydro-2H-pyran-3-yl)-1H-pyrazole-4-carboxamide, or a pharmaceutically acceptable salt thereof.

8. A compound according to claim 2, which is 3-((4-cyano-3-methoxyphenyl)amino)-1-((3R,4S)-4-cyanotetra-hydro-2H-pyran-3-yl)-1H-pyrazole-4-carboxamide, or a pharmaceutically acceptable salt thereof.

9. A compound according to claim 2, which is 3-((4-cyano-3-(2-fluoropropan-2-yl)phenyl)amino)-1-((3R,4S)-4-cyanotetrahydro-2H-pyran-3-yl)-1H-pyrazole-4-carboxamide, or a pharmaceutically acceptable salt thereof.

10. A compound according to claim 2, which is 1-((3R,4S)-4-cyanotetrahydro-2H-pyran-3-yl)-3-((3-methylbenzo[d]isoxazol-5-yl)amino)-1H-pyrazole-4-carboxamide or a pharmaceutically acceptable salt thereof.

11. A pharmaceutical composition comprising a compound of claim 1 or a pharmaceutically acceptable salt, or a stereoisomer thereof and a pharmaceutically acceptable carrier.

12. A method for the treatment of a JAK-mediated disease comprising administering to a patient in need thereof a therapeutically effective amount of a compound of claim 1 or a stereoisomer, or a pharmaceutically acceptable thereof.

13. A method of treating a condition in a mammal that can be ameliorated by the selective inhibition of a Janus kinase JAK1 relative to JAK 2 and JAK 3 which condition is selected from, arthritis, asthma and obstructive airways diseases, autoimmune diseases or disorders, and cancer comprising administering to the mammal in need of such treatment, a therapeutically effective amount of a compound according to claim 1 or a pharmaceutically acceptable salt or a stereoisomer thereof.

14. A method according to claim 13, wherein said condition is arthritis.

15. A method according to claim 14, wherein said condition is selected from rheumatoid arthritis, juvenile arthritis, and psoriatic arthritis.

16. A method according to claim 13, wherein said condition is asthma or obstructive airways diseases.

17. A method according to claim 13, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease (COPD), and emphysema.

18. A method according to claim 13, wherein said condition is autoimmune diseases or disorders.

19. A method of treating asthma in a mammal in need thereof, comprising administering a therapeutically effective amount of a compound according to claim 1 or a pharmaceutically acceptable salt or a stereoisomer, thereof.

20. A method of treating arthritis in a mammal in need thereof, comprising administering a therapeutically effective amount of a compound according to claim 1 or a pharmaceutically acceptable salt or stereoisomer, thereof.

* * * * *